(12) United States Patent
Aldoukhi

(10) Patent No.: US 8,540,513 B1
(45) Date of Patent: Sep. 24, 2013

(54) EXPANDABLE DENTAL IMPLANT WITH IMPROVED MECHANICAL RETENTION

(76) Inventor: Murtada Hassan Aldoukhi, New York, NY (US)

( * ) Notice: Subject to any disclaimer, the term of this patent is extended or adjusted under 35 U.S.C. 154(b) by 0 days.

(21) Appl. No.: 13/438,518

(22) Filed: Apr. 3, 2012

(51) Int. Cl.
A61C 8/00 (2006.01)

(52) U.S. Cl.
USPC .......................................... 433/173; 433/172

(58) Field of Classification Search
USPC .................. 433/172–176, 201.1; 606/63, 68, 606/313, 326; 411/340, 344
See application file for complete search history.

(56) References Cited

U.S. PATENT DOCUMENTS

| | | | | |
|---|---|---|---|---|
| 2,224,023 A | * | 12/1940 | Sayen et al. | 411/342 |
| 2,601,803 A | * | 7/1952 | Newman | 411/80.1 |
| 2,685,877 A | * | 8/1954 | Dobelle | 623/23.11 |
| 3,708,883 A | | 1/1973 | Flander | |
| 5,052,930 A | | 10/1991 | Lodde et al. | |
| 5,141,435 A | * | 8/1992 | Lillard | 433/176 |
| 5,439,381 A | | 8/1995 | Cohen | |
| 5,470,230 A | | 11/1995 | Daftary et al. | |
| 5,810,820 A | * | 9/1998 | Santori et al. | 606/63 |
| 5,890,902 A | | 4/1999 | Sapian | |
| 5,984,681 A | | 11/1999 | Huang | |
| 6,004,088 A | * | 12/1999 | Hunt | 411/344 |
| 6,332,778 B1 | | 12/2001 | Choung | |
| 6,450,812 B1 | | 9/2002 | Laster et al. | |
| 7,857,840 B2 | * | 12/2010 | Krebs et al. | 606/327 |
| 2006/0194171 A1 | | 8/2006 | Lazarof | |
| 2009/0004626 A1 | | 1/2009 | Goldman | |
| 2009/0208905 A1 | | 8/2009 | Vachtenberg | |
| 2010/0304333 A1 | * | 12/2010 | Ghavidel | 433/173 |

* cited by examiner

Primary Examiner — Yogesh Patel
(74) Attorney, Agent, or Firm — Oblon, Spivak, McClelland, Maier & Neustadt, L.L.P.

(57) ABSTRACT

A dental implant with expandable engagement portions hinged on the bottom of the implant. The expandable engagement portions may be made of gold and may have a smooth or contoured outer surface and expand outward when an expander is inserted into the implant. To receive the implant, an implant site is created in the jawbone which is wider at the bottom, having a shape similar to the implant when expanded, so that once the expandable engagement portions expand outward, they fill the bottom of the implant site and thereby result in strong mechanical engagement between the implant and the jawbone. The implant is further anchored by horizontal anchoring apparatus configured for insertion into the bone and the implant. Each of the horizontal anchoring apparatus may anchor the implant onto only one wall, making it possible to use such anchoring apparatus in the event that a wall is missing.

9 Claims, 8 Drawing Sheets

EXPANDABLE DENTAL IMPLANT WITH IMPROVED MECHANICAL RETENTION

GRANT OF NON-EXCLUSIVE RIGHT

This application was prepared with financial support from the Saudia Arabian Cultural Mission, and in consideration therefore the present inventor(s) has granted The Kingdom of Saudi Arabia a non-exclusive right to practice the present invention.

BACKGROUND

1. Field of the Disclosure

This invention relates to dental implants for anatomical restoration operations and surgeries. More specifically, this invention relates to dental implants with horizontal anchors and/or expandable root portions configured to improve mechanical retention. Additionally, this invention relates to a method of inserting a dental implant, and a bone structure that includes the dental implant.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

A dental implant is an artificial tooth root, typically of a cylindrical shape, which is placed into the jawbone to hold a replacement tooth or bridge. The placement of an implant requires creation of a site in the patient's jawbone for receiving the implant. The implant site is created by precision drills. The dental implant is then threadedly fitted or press-fitted in the implant site. However, the mechanical engagement between the bone and the dental implant at the time of insertion is generally inadequate to support an artificial tooth or prosthesis.

To alleviate this problem, a variable amount of time is allowed for the bone to grow around and into the implant, and thereby enhance the anchoring of the dental implant, which can then support an artificial tooth or bridge. This physiological process of the metal fusing with a living bone is called osseointegration.

Most dental implants are made of titanium or of a titanium alloy, due to the biocompatibility and high rate of osseointegration of titanium. Osseointegration typically takes 4 to 6 months. Any strain on or movement of the implant during this time can inhibit or prevent successful osseointegration. The time period required for osseointegration is uncomfortable for the patient due to its length, the requirement for multiple office visits, and the unpleasant cosmetic appearance.

Besides the need for osseointegration, the most basic dental implant technology has other shortcomings. As we age, the sinus cavity gets larger due to the natural loss of bone. This loss of bone results in reduced thickness in the upper jawbone, and complicates the implant process in that region. A minimum bone thickness of 1.5 millimeters is needed all around the implant to facilitate the implant process for a conventional implant support and anchorage. Additionally, the implant site should be a minimum of 1-2 millimeters away from any vital structure such as nerves. This might necessitate a bone graft procedure which can take an additional 6 to 9 months, adding to the total implant procedure time and of course increasing the overall cost.

Having a missing tooth for several months creates potential further problems such as shifting and chipping of adjacent teeth and problems with the temporomandibular joint (TMJ). TMJ is the area directly in front of the ear on either side of the head where the upper jaw (maxilla) and lower jaw (mandible) meet. The TMJ is used throughout the day to move the jaw, especially in biting and chewing, talking, and yawning. It is one of the most frequently used joints of the body. When a tooth is missing for an extended period of time, a patient might develop a new chewing habit in order to avoid the missing tooth. This can lead to a TMJ disorder.

Yet another potential problem is bone resorption. Bone resorption is the process by which osteoclasts break down bone and release the minerals, resulting in a transfer of calcium from bone fluid to the blood. Bone resorption is noticeable during the time required for osseointegration, due to the lack of pressure normally applied by the extracted tooth onto the bone tissue.

Expandable implants have been suggested and used to enhance the mechanical engagement between the dental implant and the jawbone, as in e.g., Flander (U.S. Pat. No. 3,708,883), Daftary et al. (U.S. Pat. No. 5,470,230) (hereinafter Daftary), Choung (U.S. Pat. No. 6,332,778), Lazarof (U.S. Pub. No. 2006/0194171), Vachtenberg (U.S. Pub. No. 2009/0208905), and Ghavidel (U.S. Pub. No. 2010/0304333); each of which is incorporated here by reference in its entirety such that the structural components and architectural features such as surface structures and attachment mechanisms described therein are a part of the present disclosure.

Generally, in expandable implants, the outer diameter of the implant relative to the wall of the site is adjustable. By providing a controlled amount of lateral expansion, the outer surface of the implant is in pressured, frictional engagement with the jawbone.

To provide more secure and stable mounting of the implant and allow the installation of the prosthesis and loading without the extensive waiting period, dental implants with additional support members or anchors may be used. Anchors also allow use of shorter implants which may eliminate the need for supplementary bone graft surgery. Several embodiments of anchors have been suggested in the prior art, as in e.g., Sapian (U.S. Pat. No. 5,890,902), Huang (U.S. Pat. No. 5,984,681), Laster et al. (U.S. Pat. No. 6,450,812) (hereinafter Laster), and Goldman (U.S. App. No. 2009/0004626); each of which is incorporated here by reference in its entirety such that the structural components and architectural features such as surface structures and attachment mechanisms described therein are a part of the present disclosure. In particular, Laster provides a detailed summary of several issues regarding dental implants, and a review of related technology.

SUMMARY

This disclosure relates to an improved apparatus and method to address the aforementioned issues, namely the need for dental implants that are effective without osseointegration.

According to a preferred embodiment, a dental implant is disclosed with expandable engagement portions hinged on the bottom of the implant. The expandable engagement portions have smooth or contoured outer surfaces and expand outward when an expander is inserted into the implant.

To receive the implant, an implant site is created in the jawbone which is wider at the bottom. The bottom of the implant site has similar shape as the expandable engagement portions so that once the expandable engagement portions expand outward the bottom of the implant site is filled resulting in strong mechanical engagement between the implant and the jawbone.

According to a preferred embodiment, the expandable engagement portions are made of gold which is compatible with human body and also can be easily formed into a desired shape.

According to a preferred embodiment, the implant is anchored by one or more horizontal anchoring apparatus configured for insertion into the bone and the implant. Each of the horizontal anchoring apparatus anchors the implant onto at least one wall.

In another embodiment, the horizontal anchoring apparatus anchors onto only one wall, making it possible to use such anchoring apparatus in the event that a wall is missing.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figures 1A, 1B:
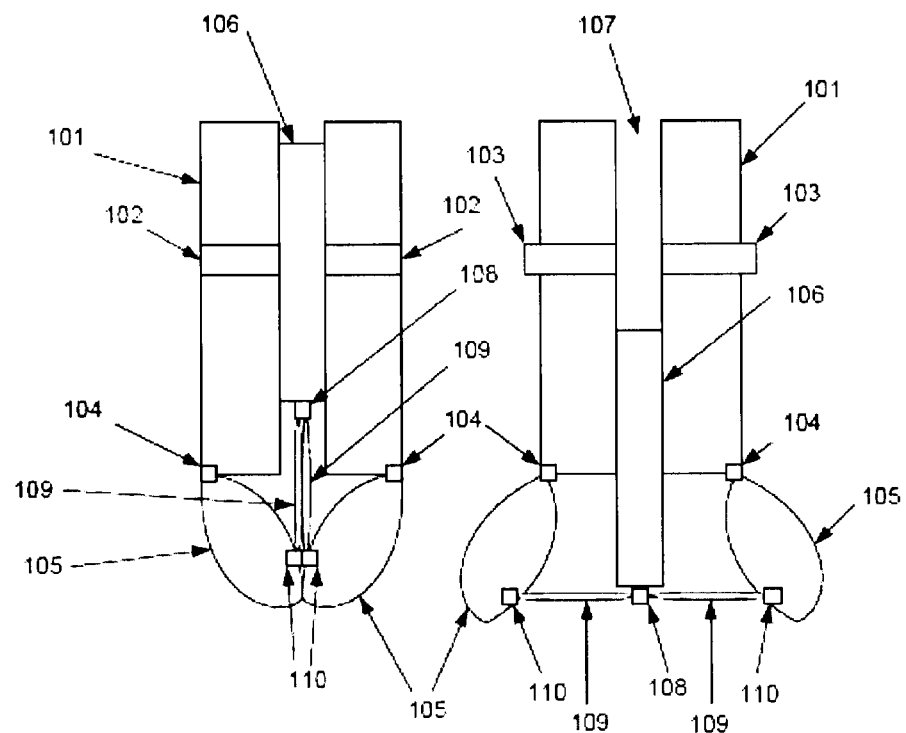
FIGS. 1A, 1B, and 1C respectively illustrate perspective views of a first embodiment of an implant before insertion and after insertion and an implant site created in a jawbone to receive the implant.

Referring now to the drawings, wherein like reference numerals designate identical or corresponding parts throughout the several views.

Figure 1C:
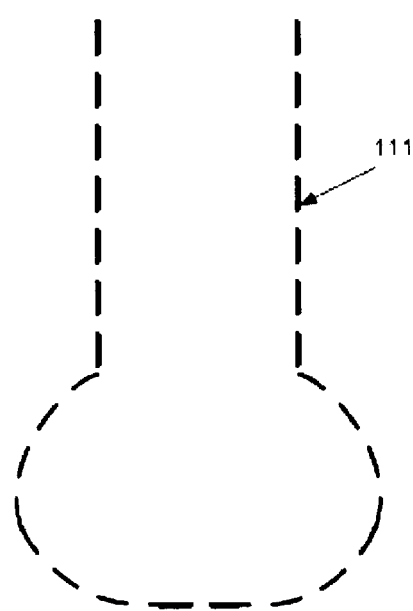

FIGS. 1A, 1B, and 1C respectively illustrate perspective views of an implant before insertion and after insertion, and an implant site created in a jawbone to receive the implant. The implant has a central core body 101 which has one or more horizontally oriented cavities 102 around it for the insertion of one or more anchors 103. Each anchor when inserted, preferably extends at most up to the vertical cavity of the central core body, thereby needing only one wall around the implant to anchor the central core body onto. The bottom edge of the central core body 101 can receive a retaining and pivoting mechanism from a plurality of hinges 104 on a plurality of expandable engagement portions 105. The expandable engagement portions are expanded by an expander 106 placed in a vertically oriented cavity 107 along the central axis of the central core body 101. The expander 106 and the expandable engagement portions 105 are connected by means of a lever connection mechanism 108 at the bottom of the expander 106, and a plurality of expansion levers 109 which are chained to the expander on one side, and to a plurality of engagement portion connection mechanisms 110 on the opposite side, such engagement portion connection mechanisms 110 being mounted at the bottom of the expandable engagement portions 105. Detail description of the lever connection mechanism and the engagement portion connection mechanisms will be provided later.

As shown in FIG. 1A, before the insertion of the implant, the expander 106 is positioned at the top of the vertically oriented cavity 107. The expansion levers 109 are folded and pulled into the vertically oriented cavity 107, causing the expandable engagement portions 105 to be pulled toward each other. As shown in FIG. 1B, once the implant is inserted, the expander 106 is forced down the vertically oriented cavity 107, causing the expansion levers 109 to move away from each other, and consequently, causing the expandable engagement portions 105 to expand.

The shape of the bottom of the dental implant after insertion and expansion of the expandable engagement portions 105, at least partially fills an implant site 111 created in a jawbone to receive the implant, as shown in FIG. 1C.

Preferably, an external surface of the central core body 101 is threaded to increase the surface area in contact with cancellous bone tissue and thereby enhance the support of the bone tissue around the central core body. The threaded central core body is screwed into the implant site to self-tap itself and carve an internal thread into the cancellous bone tissue, so as to ensure a tight fit.

Preferably, the horizontally oriented cavities 102 have a threaded surface. In this case, the anchors 103 are typically formed as screws or pins matching the threaded surface of the horizontally oriented cavities, and are arranged for insertion into the jawbone. After insertion of the central core body, the anchors are screwed into the bone and into the horizontally oriented cavities.

Alternatively or additionally, the anchoring mechanism may be accomplished by the use of brackets attaching the anchors onto the central core body.

Alternatively or additionally, the anchors may be glued or cemented onto the central core body.

Preferably, a saline solution, curable composition, or cement is injected through a nozzle within the anchors at the time of the insertion to fill the imperfections of the horizontally oriented cavities. The same injection mechanism may be adopted during the insertion of the central core body or the expander.

Alternatively, the implant site may be initially filled with a saline solution before the insertion of the central core body to avoid packets of air and to push out impurities during the implant insertion procedure.

Preferably, the expandable engagement portions are made of biocompatible material, specifically gold, and have a smooth or contoured outer surface. Gold is the preferred material because it is easy to manipulate which makes it possible to form the expandable engagement portions into a desired shape. The particular gold alloy to be used is as is used and well known in the art.

Preferably, the implant site is created by a first device to drill a whole in the jawbone, and a second device to create a wider space at the bottom of the drilled whole.

Preferably, before the insertion of the dental implant, the expandable engagement portions are held together by temporary attachment means such as glue or a piece of plastic. Such temporary attachment means break upon insertion of the expander.

Figures 2A, 2B:
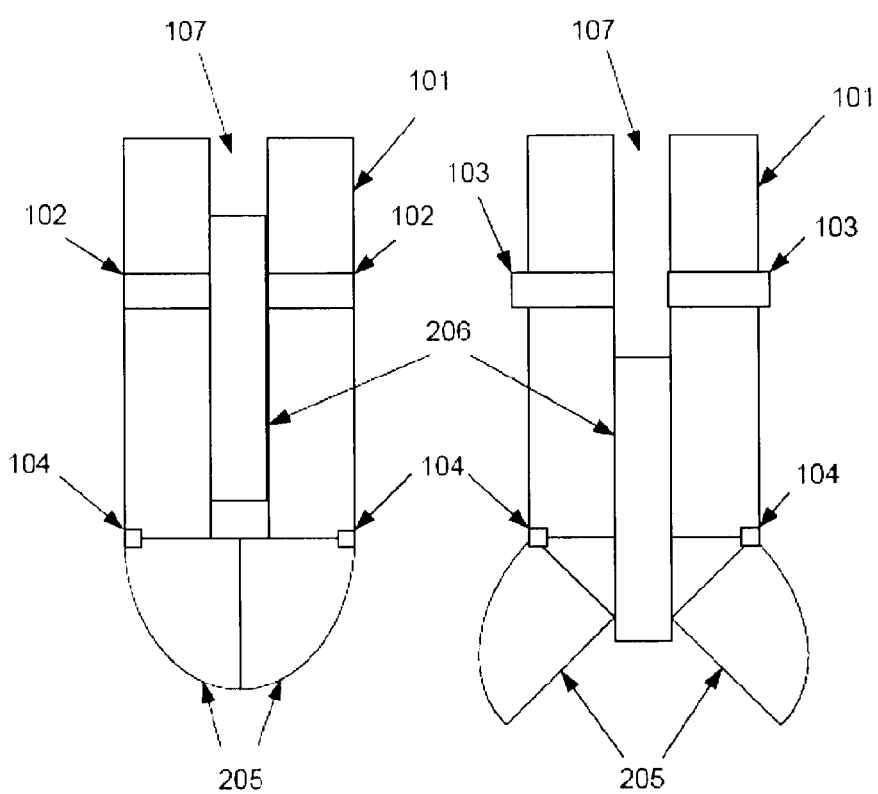
FIGS. 2A and 2B respectively illustrate perspective views of a second embodiment of an implant before insertion and after insertion.

FIGS. 2A and 2B respectively illustrate perspective views of a second embodiment of an implant before insertion and after insertion. In this embodiment, a plurality of simple expandable engagement portions 205 are expanded by the insertion of a simple expander 206. The expansion mechanism in this embodiment is simpler than the previous embodiment. However, the previous embodiment provides further expansion of the expandable engagement portions by utilizing the expansion levers and the required connection mechanisms on both sides of the levers.

In the case of dehiscence, a subset of the horizontally oriented cavities is determined, and only those horizontally oriented cavities belonging to this subset will be used for anchoring. Other health conditions that prohibit effective use of a horizontally oriented cavity can be similarly addressed.

Figures 3A, 3B:
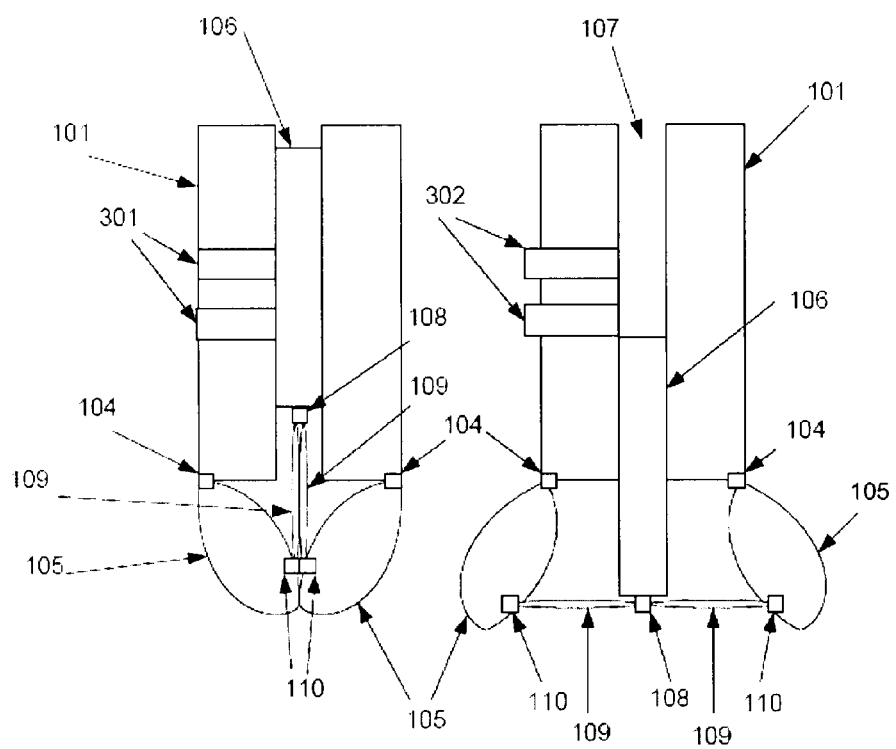
FIGS. 3A and 3B respectively illustrate perspective views of a third embodiment of an implant before insertion and after insertion.

FIGS. 3A and 3B respectively illustrate perspective views of a third embodiment of an implant before insertion and after insertion. In this embodiment, a plurality of stacked or staged horizontally oriented cavities 301 receive a plurality of stacked or staged anchors 302, only on one side of the central core body. The horizontally oriented cavities are on the same side, but at vertically different heights on the central core body. In the event that only one side of the implant is available for anchoring, having multiple anchoring apparatus on one side ensures sufficient support of the available bone.

Figures 4A, 4B:
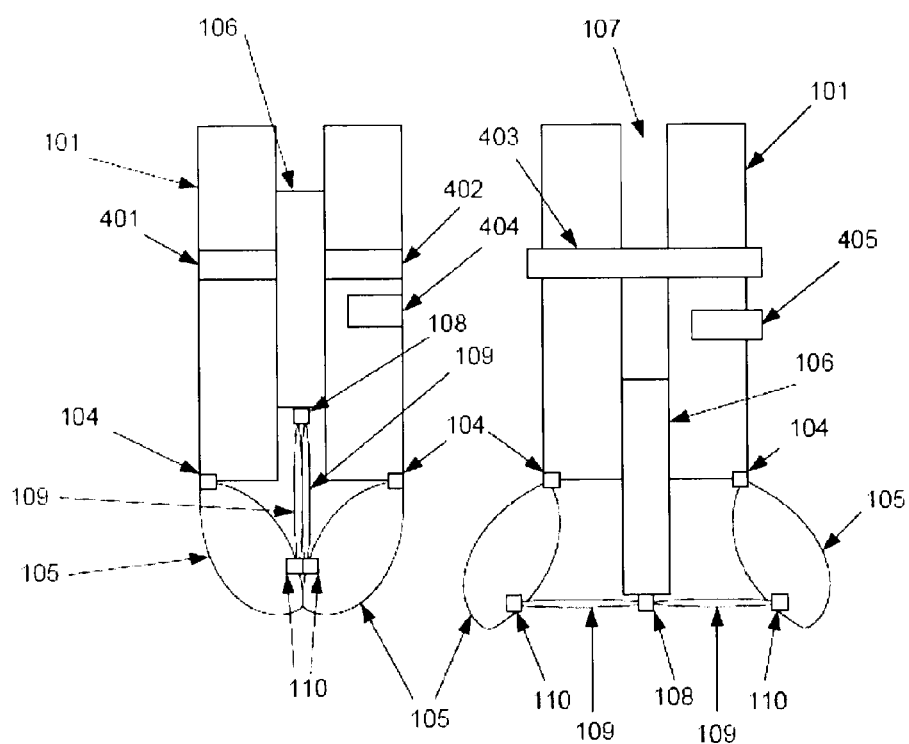
FIGS. 4A and 4B respectively illustrate perspective views of a fourth embodiment of an implant before insertion and after insertion.

FIGS. 4A and 4B respectively illustrate perspective views of a fourth embodiment of an implant before insertion and after insertion. In this embodiment, a pair of paired horizontally oriented cavities 401 receive a bi-cortical anchor 403 which anchors the central core body onto two opposite walls. The bi-cortical anchor can be inserted only after the expander is forced down the vertically oriented cavity. FIGS. 4A and 4B also show a short horizontally oriented cavity 404 and a short anchor 405 that do not extend as far as the middle of the central core body. This fourth embodiment is shown to emphasize that the horizontally oriented cavities can be of various lengths, and can anchor onto one or two walls around the central core body.

Figures 5A, 5B, 5C:
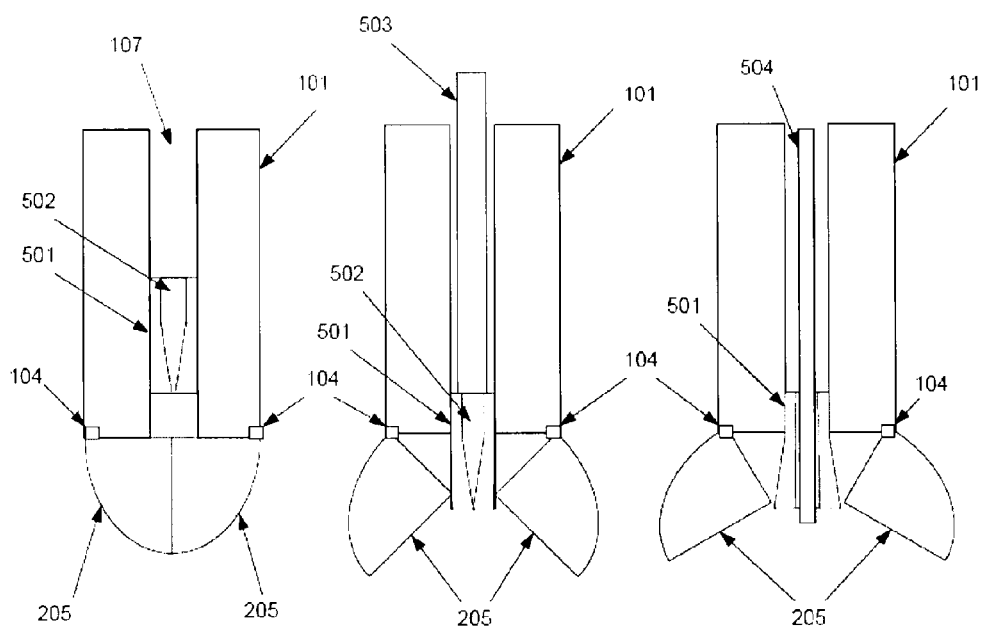
FIGS. 5A, 5B, and 5C respectively illustrate perspective views of a fifth embodiment of an implant before insertion, during insertion, and after insertion.

FIGS. 5A, 5B, and 5C respectively illustrate perspective views of a fifth embodiment of an implant before insertion, during insertion, and after insertion. This embodiment illustrates a two-step expansion mechanism. A conical expander 501 is used for the expansion of the simple expandable engagement portions 205. The conical expander has vertical slits along the bottom half and has a conical cavity 502 which is narrower at the bottom. The conical expander is forced down the vertically oriented cavity by means of a first tool 503. Then, as shown in FIG. 5C, a second tool 504 is inserted into the conical cavity of the conical expander to cause expansion of the conical expander along the slits. Expansion of the slitted bottom of the conical expander in turn causes further expansion of the simple expandable engagement portions 205.

Figures 6A, 6B, 6C:
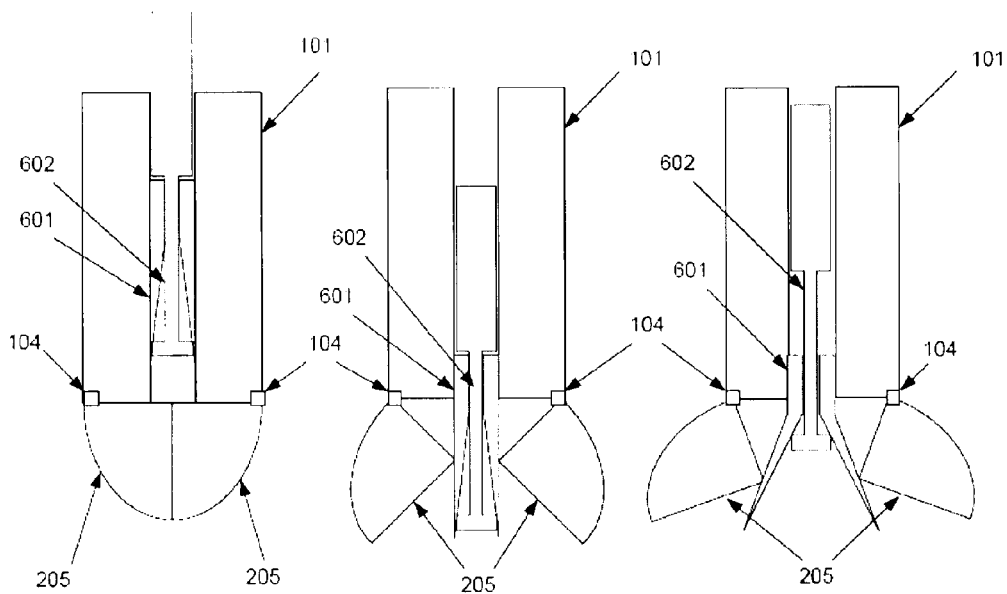
FIGS. 6A, 6B, and 6C respectively illustrate perspective views of a sixth embodiment of an implant before insertion, during insertion, and after insertion.

FIGS. 6A, 6B, and 6C respectively illustrate perspective views of a sixth embodiment of an implant before insertion, during insertion, and after insertion. This embodiment illustrates another two-step expansion mechanism. A two-piece expander 601 is used for the expansion of the simple expandable engagement portions 205. The two-piece expander has vertical slits along the bottom half, and has a central piece 602 which stays loosely attached to the two-piece expander. The central piece is wider at the bottom, very narrow in the middle, and wider at the top. The two-piece expander is forced down the vertically oriented cavity by forcing down the central piece. This causes the first step of the expansion as shown in FIG. 6B. Then, as shown in FIG. 6C, the central piece is pulled up. This causes the wider bottom of the central piece to move up, and thereby cause expansion of the bottom walls of the two-piece expander along the vertical slits. Expansion of the slitted bottom of the two-piece expander in turn causes further expansion of the simple expandable engagement portions 205.

In another embodiment, the top surface of the central piece may be adapted to receive a sliding engagement mechanism so a tool could be used to engage with and pull up the central piece.

Other expansion mechanisms known in the art can be adopted for the expansion of an expander with split bottom. In one such embodiment, the split bottom expander is hollow and receives a solid shaft with a wedge shaped base inserted from the bottom of the expander. After insertion of the implant, the solid shaft is drawn upwardly through the implant so that the wedge shaped base can cause the split bottom of the expander to expand outwardly.

Figures 7A, 7B:
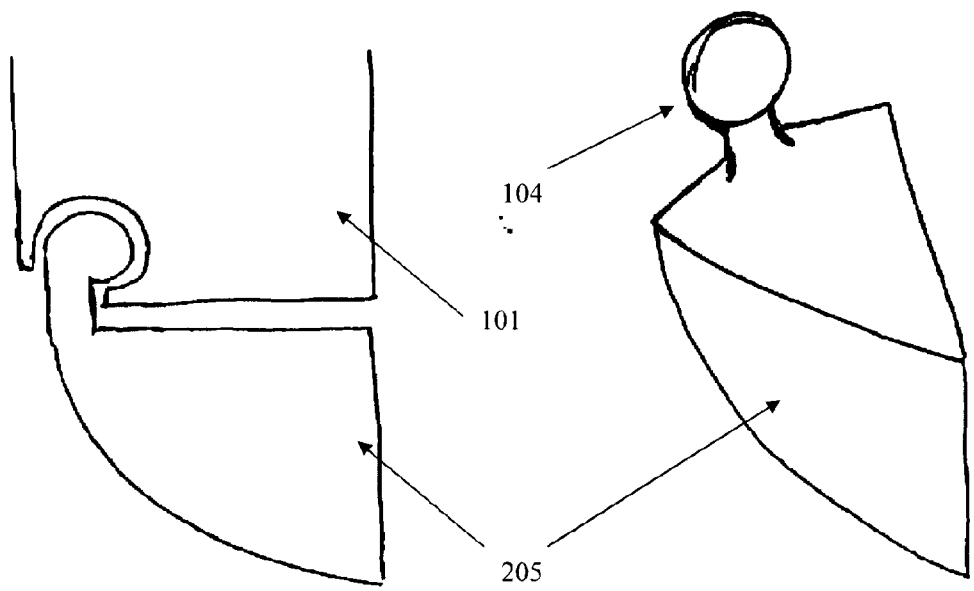
FIGS. 7A and 7B illustrate perspective views of a hinging mechanism between an expandable engagement portion and a central core body.

FIGS. 7A and 7B illustrate perspective views of a hinging mechanism between a simple expandable engagement portion 205 and a central core body 101. The hinge 104 is a ball shaped protrusion on the top surface of the simple expandable engagement portion. This hinging mechanism may be alternatively used to hinge the simple expandable engagement portions on the bottom edge of the central core body.

Another embodiment can be realized by a T-shaped hinging mechanism. The T-shaped hinging mechanism includes a longitudinal bar and a transverse bar formed into a substantially T-shape extending from the top surface of an expandable engagement portion.

Figure 8:
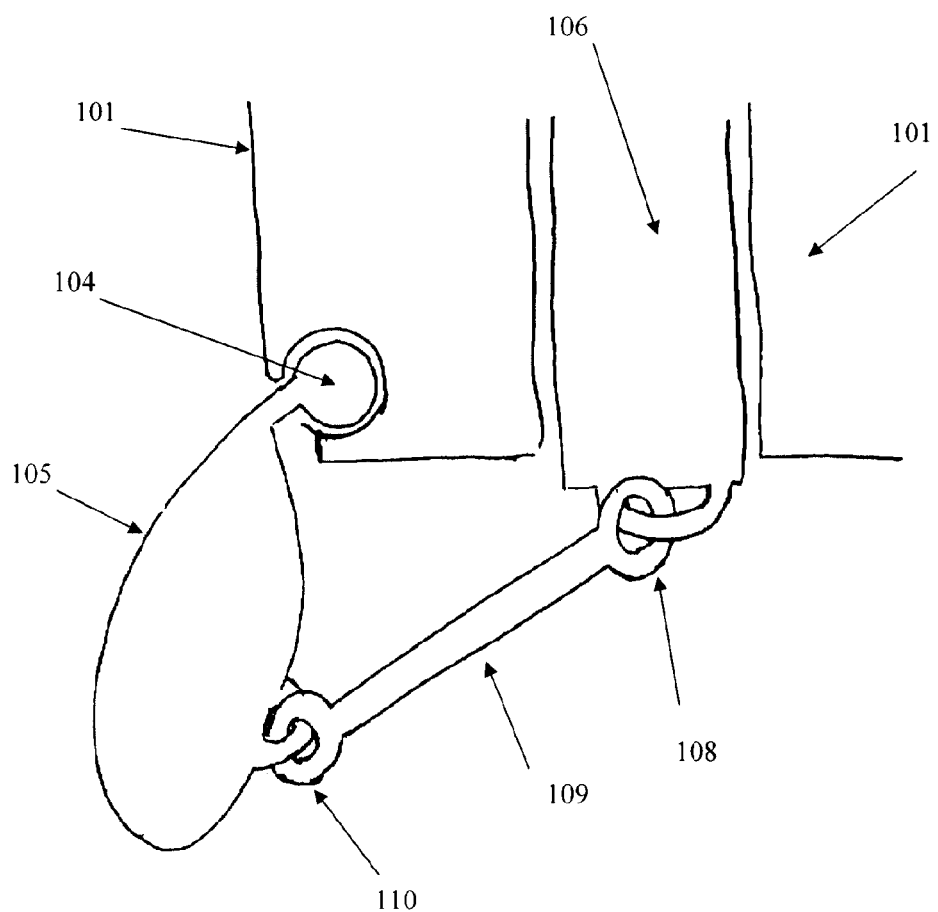
FIG. 8 illustrates perspective views of a connection mechanism between an expandable engagement portion and a lever, and between the lever and an expander.

FIG. 8 illustrates perspective views of a connection mechanism between an expandable engagement portion and a lever, and between the lever and an expander. The lever connection mechanism 108 is a loop built onto one end of the lever which connects to another loop built onto the bottom of the expander. The expandable engagement portion connection mechanism 110 is a loop built onto the other side of the lever 109 which connects to another loop built onto the bottom of the expandable engagement portion.

Other embodiments can be realized by replacing the connection mechanism with a hinging mechanism as described for the engagement of the central core body with the simple expandable engagement portions.

In yet another embodiment, the expandable engagement portions are connected to the central core body via loops, while the lever is hinged onto the expander, so a pivoting mechanism is provided by the hinging of the levers onto the expander, thereby eliminating the need for a pivoting mechanism between the central core body and the expandable engagement portions.

Additional embodiments may be realized by adding a variety of supplementary anchoring features known in the art to any of the above disclosed embodiments. For example, a generally vertically projected anchoring pin may be incorporated within any of the disclosed embodiments to further enhance the mechanical engagement by interconnecting the implant with the alveolar bone of the patient. Such anchoring pin may be designed such that it projects downwardly into the alveolar bone.

The apparatus and method for attaching a tooth prosthesis or bridge to the central core body may be as is known in the art, or as disclosed in any of the incorporated references. Various embodiments may thereby be realized depending on the tooth prosthesis or bridge attachment method chosen.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A dental implant comprising:
   a central core body with a vertically oriented cavity extending from the top of the central core body through the bottom along a central axis of the central core body;
   a plurality of horizontally oriented cavities on the central core body;
   a plurality of anchors for insertion in a subset of said horizontally oriented cavities;
   a plurality of expandable engagement portions hinged at the bottom of the central core body; and
   an expander in said vertically oriented cavity wherein said expander expands said expandable engagement portions upon an insertion of the expander; wherein the expander is configured to expand and retract the expandable engagement portions into an implant site, wherein the expandable engagement portions are configured to have a diameter greater than the diameter of the central core body.

2. The dental implant of claim 1 wherein said central core body has a threaded outer surface.

3. The dental implant of claim 1 wherein said vertically oriented cavity has a threaded surface.

4. The dental implant of claim 3 wherein said expander has a threaded surface matching the threaded surface of said vertically oriented cavity.

5. The dental implant of claim 1 wherein said expander has a tool engaging surface for rotating said expander.

6. The dental implant of claim 1 wherein said expander and said expandable engagement portions are connected by a plurality of levers, each lever in loose mechanical engagement with the expander on one side, and in loose mechanical engagement with one of the expandable engagement portions on the opposite side, such that insertion of the expander causes the levers to move away from each other and push the expandable engagement portions to expand.

7. The dental implant of claim 1 wherein said plurality of expandable engagement portions are made of a biocompatible material.

8. The dental implant of claim 7 wherein said biocompatible material is gold.

9. A method of inserting a dental implant comprising:
   creating an implant site in a jawbone;
   inserting the dental implant of claim 1; and
   inserting said expander to cause said plurality of expandable engagement portions to expand.

* * * * *